United States Patent
Haddad et al.

(10) Patent No.: US 9,029,540 B2
(45) Date of Patent: May 12, 2015

(54) RUTHENIUM CATALYSTS AND THEIR USE FOR ASYMMETRIC REDUCTION OF KETONES

(71) Applicants: Nizar Haddad, Danbury, CT (US); Heewon Lee, Parsippany, NJ (US); Bo Qu, Brookfield, CT (US); Sonia Rodriguez, New Milford, CT (US); Chris Hugh Senanayake, Brookfield, CT (US)

(72) Inventors: Nizar Haddad, Danbury, CT (US); Heewon Lee, Parsippany, NJ (US); Bo Qu, Brookfield, CT (US); Sonia Rodriguez, New Milford, CT (US); Chris Hugh Senanayake, Brookfield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/313,085

(22) Filed: Jun. 24, 2014

(65) Prior Publication Data
US 2015/0005500 A1    Jan. 1, 2015

Related U.S. Application Data

(60) Provisional application No. 61/841,629, filed on Jul. 1, 2013.

(51) Int. Cl.
| | |
|---|---|
| C07F 15/00 | (2006.01) |
| C07D 405/04 | (2006.01) |
| B01J 31/22 | (2006.01) |
| C07D 215/20 | (2006.01) |
| C07D 209/04 | (2006.01) |
| C07D 333/54 | (2006.01) |
| C07D 307/79 | (2006.01) |
| C07C 29/145 | (2006.01) |
| C07D 231/56 | (2006.01) |
| B01J 23/46 | (2006.01) |
| B01J 31/24 | (2006.01) |
| C07C 29/156 | (2006.01) |
| C07B 53/00 | (2006.01) |

(52) U.S. Cl.
CPC ........... *B01J 31/2295* (2013.01); *C07D 215/20* (2013.01); *C07D 209/04* (2013.01); *C07D 333/54* (2013.01); *C07D 307/79* (2013.01); *C07C 29/145* (2013.01); *C07D 231/56* (2013.01); *B01J 23/462* (2013.01); *B01J 31/24* (2013.01); *C07C 29/156* (2013.01); *C07B 53/00* (2013.01); *C07F 15/0046* (2013.01); *C07F 15/0053* (2013.01)

(58) Field of Classification Search
USPC .................... 546/2, 10, 167; 556/13
See application file for complete search history.

(56) References Cited

U.S. PATENT DOCUMENTS 8,552,212 B2 * 10/2013 Qu et al. ............ 556/18

FOREIGN PATENT DOCUMENTS

WO    2011056737 A1    5/2011

OTHER PUBLICATIONS

International Search Report for PCT/US2014/043813 mailed Aug. 28, 2014.

Rodriguez, Sonia et al. "Amine-Tunable Ruthenium Catalysts for Asymmetric Reduction of Ketones" Advanced Synthesis & Catalysis (2014) vol. 356, pp. 301-307.

* cited by examiner

*Primary Examiner* — Charanjit Aulakh
(74) *Attorney, Agent, or Firm* — Michael P. Morris; Usha R. Patel

(57) ABSTRACT

Disclosed are novel ruthenium compounds of formula (Ia) and (Ib):

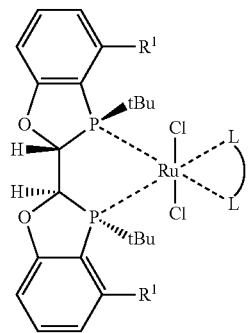

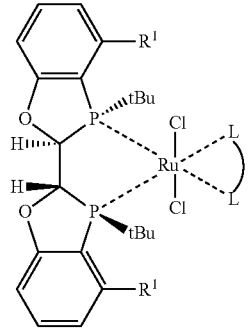

wherein $R^1$ and the moiety L⌒L are defined herein. Also disclosed is a process for using these novel ruthenium compounds as catalysts for asymmetric hydrogenation and transfer hydrogenation of ketones with high reactivities and excellent selectivities.

24 Claims, No Drawings

RUTHENIUM CATALYSTS AND THEIR USE FOR ASYMMETRIC REDUCTION OF KETONES

TECHNICAL FIELD

The invention relates to a new family of amine-tunable ruthenium catalysts based on chiral bisdihydrobenzooxaphosphole ligands (BIBOP ligands). The catalysts are useful for asymmetric hydrogenation and transfer hydrogenation of a variety of highly challenging ketones, including heteroaryl cyclic ketones.

BACKGROUND OF THE INVENTION

Asymmetric reduction of ketones is a key transformation in the pharmaceutical industry for the preparation of enantiomerically pure alcohols, particularly those bearing heterocycles (see, e.g., *The handbook of Homogeneous Hydrogenation* (Eds.: J. G. De Vries, C. J. Elsevier), Willey-VCH, Weinheim, 2007; and C. Hedberg, in *Modern Reduction Methods* (Eds.: P. G. Andersson, I. J. Munslow), WILEY-VCH, Weinheim, 2008, pp. 109-134). Chiral RuCl$_2$(diphosphine)(diamine) complexes pioneered by Noyori and co-workers catalyze highly efficient asymmetric hydrogenation of a wide array of ketones to afford the corresponding alcohols (see, e.g., T. Ohkuma et al., *J. Am. Chem. Soc.* 1995, 117, 2675-2676; H. Doucet et al., *Angew. Chem. Int. Ed.* 1998, 37, 1703-1707; and T. Ohkuma et al., *J. Am. Chem. Soc.* 1998, 120, 13529-13530). Despite the variety of catalysts described in the literature (see, e.g., K. Mikami et al., *Angew. Chem. Int. Ed.* 1999, 38, 495-497; M. J. Burk et al., *Org. Lett.* 2000, 2, 4173-4176; and J. Wu et al., *Chem. Eur. J.* 2003, 9, 2963-2968); very few ruthenium catalysts have been able to hydrogenate cyclic ketones such as 1-tetralones (see, e.g., T. Ohkuma et al., *Org. Lett.* 2004, 6, 2681-2683; and T. Touge et al., *J. Am. Chem. Soc.* 2011, 133, 14960-14963). Furthermore, examples of heteroaryl cyclic ketones hydrogenation are extremely rare. To our knowledge, the only reported asymmetric hydrogenation of a heteroaryl cyclic ketone utilized a Ru-BINAP complex with a 1,4-diamine derived from natural mannitol for the reduction of 4,5,6,7-tetrahydrofuran-4-one (see T. Ohkuma et al, *Org. Lett.* 2004, 6, 2681-2683).

In addition, only a few chiral catalysts have been reported to exhibit turnover numbers (TON, molar ratio of converted substrate to catalyst) over 100,000 with simple aryl methyl ketones, while most of the reported chiral catalysts have TON lower than 1000, making these catalytic systems unsuitable for industrial applications (see, e.g., K. Tsutsumi et al., *Org. Proc. Res. Develop.* 2009, 13, 625-628). In the synthesis of potential cholesterylester transfer protein (CETP) inhibitors, we needed to perform an asymmetric reduction of the advanced intermediate ketone of type 1 as such as depicted in Scheme 1.

Scheme 1

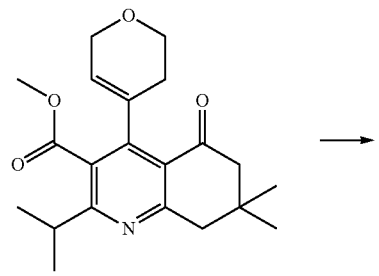

1

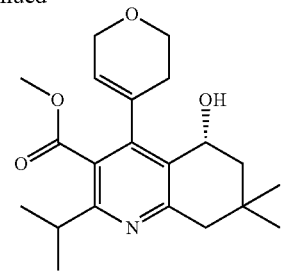

(R)-2

The reduction of 1 was initially conducted with one equivalent of borane-diethylaniline and 15-20 mol % (1R,2S)-cis-1-amino-2-indanol to afford 84% yield of (S)-2 in 96:4 er on multi-kilogram scale. Though the reaction performed well on scale-up, a greener and more efficient catalytic method was desired.

Therefore, there is a need for a more efficient method for carrying out asymmetric hydrogenations such as that shown in Scheme 1.

BRIEF SUMMARY OF THE INVENTION

The invention relates to a process of using ruthenium compounds for carrying out asymmetric reduction of ketones ("the process of the invention"). The invention also relates to novel ruthenium compounds ("the compound of the invention") which are useful for carrying out the process of the inventions.

Compounds of the Invention

In one embodiment ("embodiment 1"), the invention relates to ruthenium compounds of formulae (Ia) and (Ib):

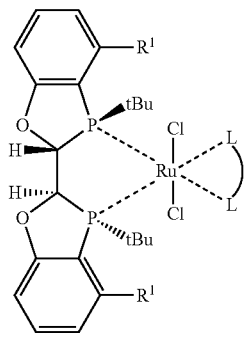

Ia

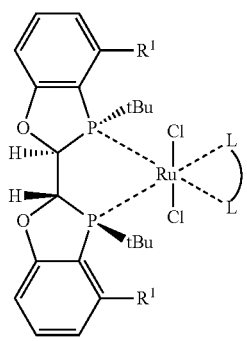

Ib wherein $R^1$ are both the same and selected from —H, —CH$_3$ and —OCH$_3$; and the moiety

L⌒L represents a diamine ligand selected from the group consisting of compounds 4, 5, 6, 7, 8, 9, and 12:

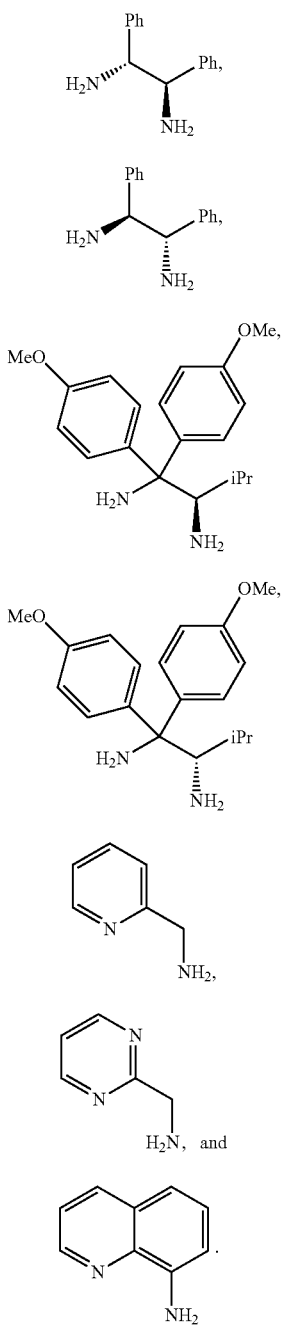

In another embodiment ("embodiment 2"), the invention relates to the compound of formula (Ia) or (Ib) according to embodiment 1, wherein $R^1$ is —H.

In another embodiment ("embodiment 3"), the invention relates to the compound of formula (Ia) or (Ib) according to embodiment 1, wherein $R^1$ is —CH$_3$.

In another embodiment ("embodiment 4"), the invention relates to the compound of formula (Ia) or (Ib) according to embodiment 1, wherein $R^1$ is —OCH$_3$.

In another embodiment ("embodiment 5"), the invention relates to the compound of formula (Ia) or (Ib) according to embodiment 1, wherein the diamine ligand is compound 4.

In another embodiment ("embodiment 6"), the invention relates to the compound of formula (Ia) or (Ib) according to embodiment 1, wherein the diamine ligand is compound 5.

In another embodiment ("embodiment 7"), the invention relates to the compound of formula (Ia) or (Ib) according to embodiment 1, wherein the diamine ligand is compound 6.

In another embodiment ("embodiment 8"), the invention relates to the compound of formula (Ia) or (Ib) according to embodiment 1, wherein the diamine ligand is compound 7.

In another embodiment ("embodiment 9"), the invention relates to the compound of formula (Ia) or (Ib) according to embodiment 1, wherein the diamine ligand is compound 9.

In another embodiment ("embodiment 10"), the invention relates to the compound of formula (Ia) or (Ib) according to embodiment 1, wherein the diamine ligand is compound 12.

In another embodiment ("embodiment 11"), the invention relates to the compound of formula (Ia) or (Ib) according to any one of embodiments 5 to 10, wherein $R^1$ is —OCH$_3$.

In another embodiment ("embodiment 12"), the invention relates to the compound of formula (Ia) or (Ib) according to embodiment 1, wherein the diamine ligand is compound 8.

In another embodiment ("embodiment 13"), the invention relates to the compound of formula (Ia) or (Ib) according to embodiment 12, wherein $R^1$ is —H.

In another embodiment ("embodiment 14"), the invention relates to the compound of formula (Ia) or (Ib) according to embodiment 12, wherein $R^1$ is —CH$_3$.

In another embodiment ("embodiment 15"), the invention relates to the compound of formula (Ia) or (Ib) according to embodiment 12, wherein $R^1$ is —OCH$_3$.

In another embodiment ("embodiment 16"), the invention relates to the compound of formula (Ia) according to any one of embodiments 1 to 15.

In another embodiment ("embodiment 17"), the invention relates to the compound of formula (Ib) according to any one of embodiments 1 to 15.

In another embodiment ("embodiment 18"), the invention relates to compound 13:

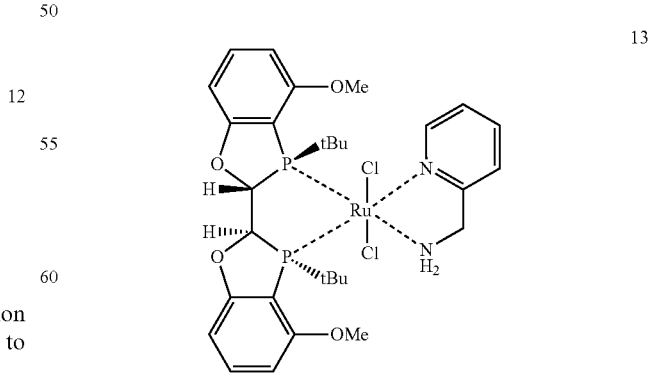

In another embodiment ("embodiment 19"), the invention relates to compound 27:

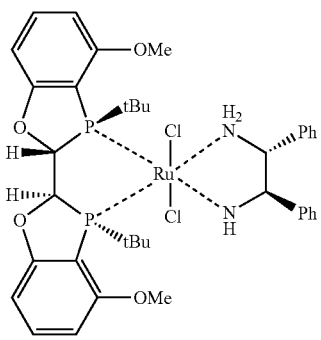

27

In another embodiment ("embodiment 20"), the invention relates to compound 28:

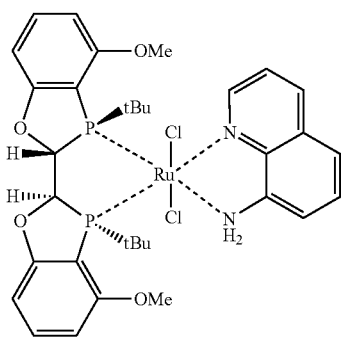

28

Processes of the Invention

As noted above, the inventors have found that the novel ruthenium compounds of the invention are useful as catalysts for carrying out asymmetric hydrogenation of ketones to provide chiral alcohols ("process of the invention"). Typically, at least about 90% of the ketone is converted to alcohol; more preferably at least about 95% of the ketone is converted to alcohol; most preferably, at least about 99% of the ketone is converted to alcohol.

The process of the invention also provides an excess of one enantiomer of the alcohol (e.g., the S-enantiomer) relative to the other enantiomer, (e.g., the R-enantiomer). Preferably, the enantiomeric ratio (er) of the isomers of the alcohol formed by the process of the invention is at least about 75:25; more preferably, the er is at least about 85:15; even more preferably, the er is at least about 90:10; still even more preferably, the er is at least about 95:5; most preferably, the er is at least about 99:1.

In one embodiment ("embodiment 21"), the invention relates to a process for making a chiral alcohol of formula X1, the process comprising reacting a ketone of formula Y1 with hydrogen in the presence of a ruthenium compound, wherein the ketone of formula Y1 and the corresponding chiral of formula X1 are as defined below:

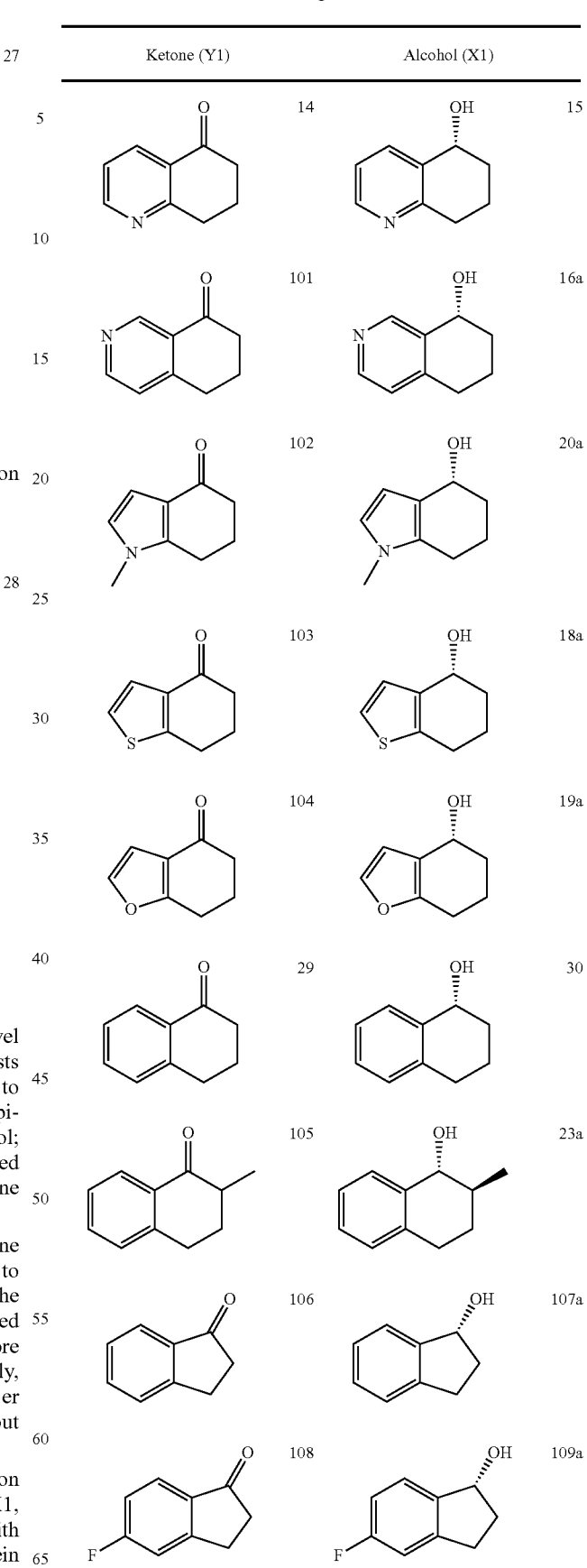

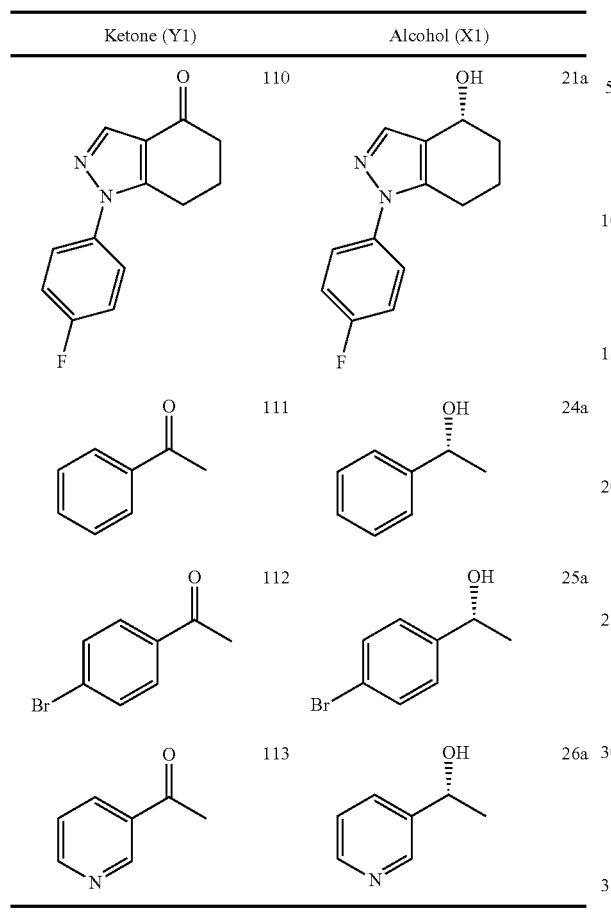

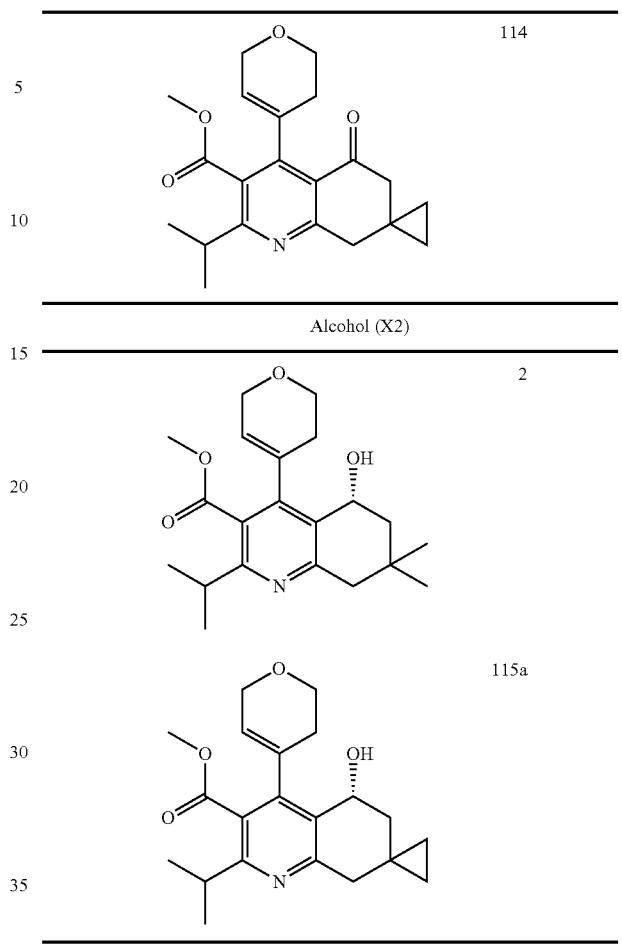

the ruthenium compound is
(a) the compound of formula (Ia) as defined in embodiment 1, wherein R¹ is —OCH₃, and the diamine ligand is compound 12; or
(b) the compound of formula (Ib) as defined in embodiment 1, wherein R¹ is —OCH₃, and the diamine ligand is compound 4, 5, 6 and 7.

In another embodiment ("embodiment 22"), the invention relates to a process for making a chiral alcohol of formula X2, the process comprising reacting a ketone of formula Y2 with hydrogen in the presence of a ruthenium compound, wherein the ketone of formula Y2 and the corresponding chiral of formula X2 are as defined below:

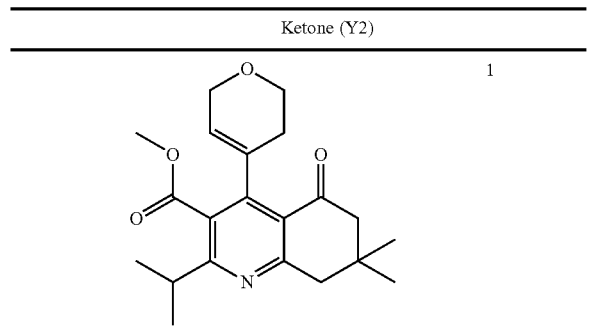

the ruthenium compound is
(a) the compound of formula (Ia) as defined in embodiment 1, wherein R¹ is —CH₃, and the diamine ligand is compound 5;
(b) the compound of formula (Ia) as defined in embodiment 1, wherein R¹ is —OCH₃, and the diamine ligand is compound 8, 9 or 12; or
(c) the compound of formula (Ib) as defined in embodiment 1, wherein R¹ is —H or —CH₃, and the diamine ligand is compound 8.

In another embodiment ("embodiment 23"), the invention relates to a process for making a chiral alcohol of formula X3, the process comprising reacting a ketone of formula Y3 with hydrogen in the presence of a ruthenium compound, wherein the ketone of formula Y3 and the corresponding chiral of formula X3 are as defined below:

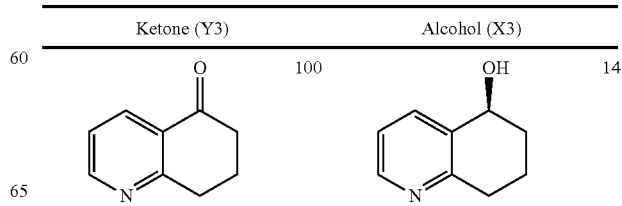

| Ketone (Y3) | | Alcohol (X3) | |
|---|---|---|---|
| 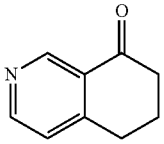 [SMILES: O=C1CCCc2ccncc21] | 101 | 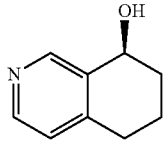 [SMILES: O[C@H]1CCCc2ccncc21] | 16 |
| 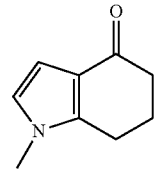 | 102 | 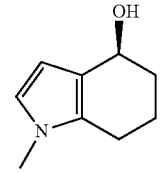 | 20 |
| 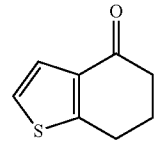 | 103 | 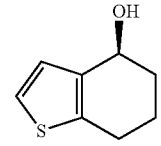 | 18 |
| 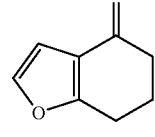 | 104 | 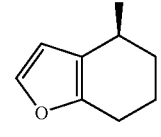 | 19 |
| 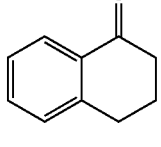 | 29 | 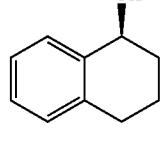 | 22 |
| 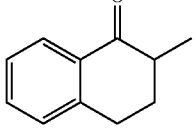 | 105 | 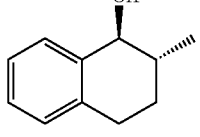 | 23 |
| 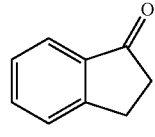 | 106 | 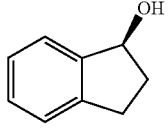 | 107 |
| 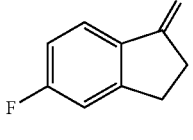 | 108 | 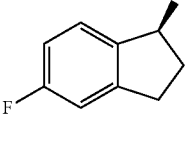 | 109 |
| 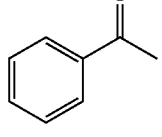 | 111 | 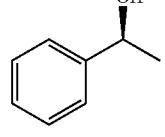 | 24 |

| Ketone (Y3) | | Alcohol (X3) | |
|---|---|---|---|
| 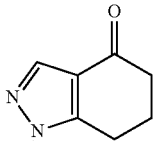 | 110 | 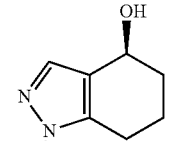 | 21 |
| 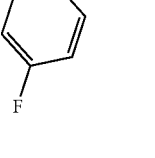 | 112 | 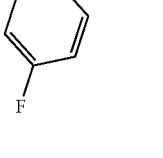 | 25 |
| 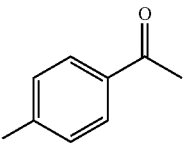 | 113 | 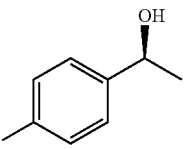 | 26 | the ruthenium compound is (a) the compound of formula (Ib) as defined in embodiment 1, wherein R¹ is —OCH₃, and the diamine ligand is compound 12; or (b) the compound of formula (Ia) as defined in embodiment 1, wherein R¹ is —OCH₃, and the diamine ligand is compound 4, 5, 6 and 7.

In another embodiment ("embodiment 24"), the invention relates to a process for making a chiral alcohol of formula X4, the process comprising reacting a ketone of formula Y4 with hydrogen in the presence of a ruthenium compound, wherein the ketone of formula Y4 and the corresponding chiral of formula X4 are as defined below:

| Ketone (Y4) | |
|---|---|
| 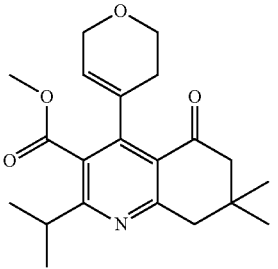 [SMILES: COC(=O)c1c(C(C)C)nc2c(c1C1=CCOCC1)C(=O)CC(C)(C)C2] | 1 |

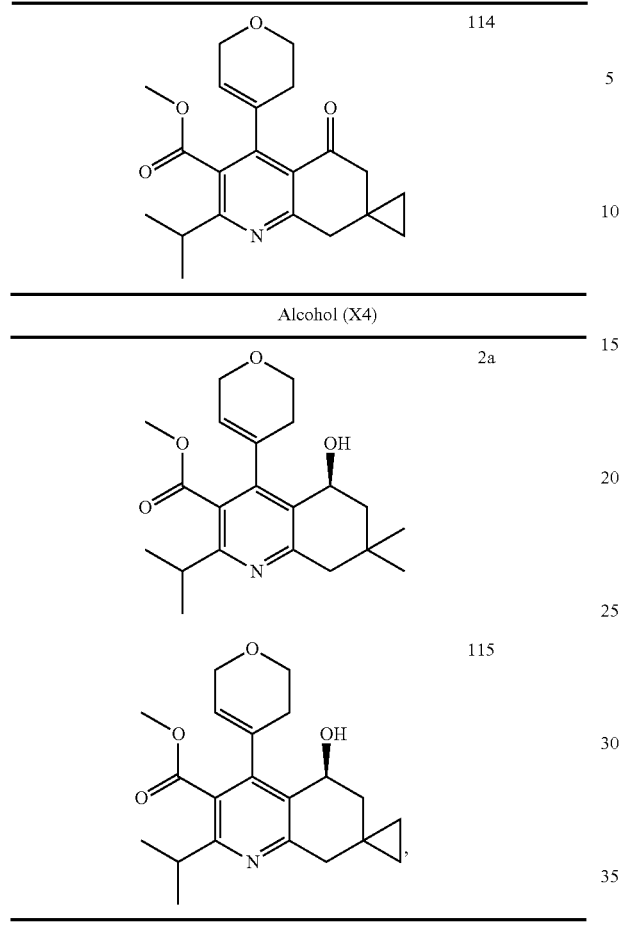

| | |
|---|---|
| | 114 |
| Alcohol (X4) | |
| | 2a |
| | 115 | and
the ruthenium compound is
(a) the compound of formula (Ib) as defined in embodiment 1, wherein $R^1$ is —$CH_3$, and the diamine ligand is compound 5;
(b) the compound of formula (Ib) as defined in embodiment 1, wherein $R^1$ is —$OCH_3$, and the diamine ligand is compound 8, 9 or 12; or
(c) the compound of formula (Ia) as defined in embodiment 1, wherein $R^1$ is —H or —$CH_3$, and the diamine ligand is compound 8.

In another embodiment ("embodiment 25"), the invention relates to the process of the invention as described in any one of the embodiments 21 to 24, wherein the ketone is contacted with the ruthenium compound prior to reaction with hydrogen.

In another embodiment ("embodiment 26"), the invention relates to the process of the invention as described in embodiment 25, wherein the ketone is contacted with the ruthenium compound and a solution of potassium tert-butoxide in tert-butanol prior to reaction with hydrogen.

In another embodiment ("embodiment 27"), the invention relates to the process of the invention as described in embodiment 26, wherein the ketone is contacted with the ruthenium compound, a solution of potassium tert-butoxide, and isopropanol prior to reaction with hydrogen.

In another embodiment ("embodiment 28"), the invention relates to the process of the invention as described in embodiment 27, wherein the ketone of formula is contacted with the ruthenium compound, and potassium tert-butoxide prior to reaction with hydrogen.

It will be understood that in the process of the invention described in any one of the embodiments 21 to 28, the ruthenium compounds can be used in isolated form or prepared in situ by reacting the corresponding precatalysts of formula (Va) or (Vb):

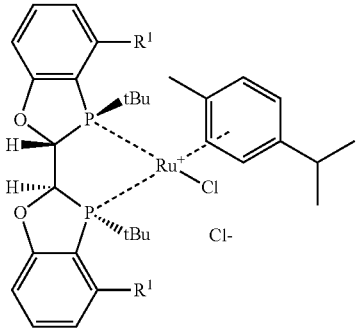

Va

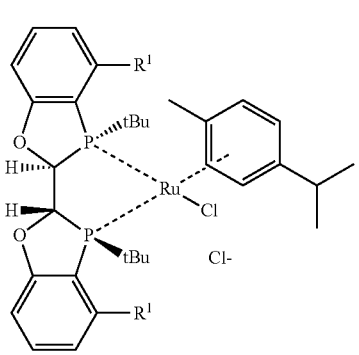

Vb with the appropriate ligand of formula 4, 5, 6, 7, 8, 9 or 12 as defined in embodiment 1; wherein $R^1$ is as defined in embodiment 1. As used herein, the term "isolated" as it relates to a Ru compound and its use in the process of the invention means that the Ru compound is substantially separated from unreacted compound of formula (Va) or (Vb) and diamine ligand prior to use.

Thus, in one embodiment ("embodiment 29"), the invention relates to the process of carrying out the asymmetric hydrogenation of ketones as described in any one of embodiments 21 to 28, wherein the compound of formula (Ia) or (Ib) is prepared in situ from the reaction of the compound of formula (Va) or (Vb), respectively, with the diamine ligand of formula 4; or the compound of formula (Ia) or (Ib) is prepared in situ from the reaction of the compound of formula (Va) or (Vb), respectively, with the diamine ligand of formula 5; or the compound of formula (Ia) or (Ib) is prepared in situ from the reaction of the compound of formula (Va) or (Vb), respectively, with the diamine ligand of formula 6; or the compound of formula (Ia) or (Ib) is prepared in situ from the reaction of the compound of formula (Va) or (Vb), respectively, with the diamine ligand of formula 7; or the compound of formula (Ia) or (Ib) is prepared in situ from the reaction of the compound of formula (Va) or (Vb), respectively, with the diamine ligand of formula 8; or the compound of formula (Ia) or (Ib) is prepared in situ from the reaction of the compound of formula (Va) or (Vb), respectively, with the diamine ligand of formula 9; or the compound of formula (Ia) or (Ib) is prepared in situ from the reaction of the compound of formula (Va) or (Vb), respectively, with the diamine ligand of formula 12.

In another embodiment ("embodiment 30"), the invention relates to a process for making the ruthenium compounds of the invention, the method comprising:

reacting a compound of formula (Va) with the diamine ligand of formula 4 to provide a compound of the invention;
reacting a compound of formula (Vb) with the diamine ligand of formula 4 to provide a compound of the invention;
reacting a compound of formula (Va) with the diamine ligand of formula 5 to provide a compound of the invention;
reacting a compound of formula (Vb) with the diamine ligand of formula 5 to provide a compound of the invention;
reacting a compound of formula (Va) with the diamine ligand of formula 6 to provide a compound of the invention;
reacting a compound of formula (Vb) with the diamine ligand of formula 6 to provide a compound of the invention;
reacting a compound of formula (Va) with the diamine ligand of formula 7 to provide a compound of the invention;
reacting a compound of formula (Vb) with the diamine ligand of formula 7 to provide a compound of the invention;
reacting a compound of formula (Va) with the diamine ligand of formula 8 to provide a compound of the invention;
reacting a compound of formula (Vb) with the diamine ligand of formula 8 to provide a compound of the invention;
reacting a compound of formula (Va) with the diamine ligand of formula 9 to provide a compound of the invention;
reacting a compound of formula (Vb) with the diamine ligand of formula 9 to provide a compound of the invention;
reacting a compound of formula (Va) with the diamine ligand of formula 12 to provide a compound of the invention; or
reacting a compound of formula (Vb) with the diamine ligand of formula 12 to provide a compound of the invention.

DETAILED DESCRIPTION OF THE INVENTION

Abbreviations

AcOH=acetic acid
ampy=2-aminomethylpyridine
amqui=8-aminoquinoline,
BINAP=(R)-(+)-(1,1'-Binaphthalene-2,2'-diyl)bis(diphenylphosphine),
i-Pr-BIMAH=2-(α-(i-propyl)methanamine)-1H-benzimidazole,
Xyl-BINAP=2,2'-bis(bis(3,5-dimethylphenyl)phosphino)-1,1'-binaphthalene,
DCM=dichloromethane,
daipen=1,1-Bis(4-methoxyphenyl)-3-methyl-1,2-butanediamine,
dpen=1,2-diphenylethane-1,2-diamine,
IPA=isopropyl alcohol,
RUCY™-XylBINAP=Chloro {(R)-(+)-2,2'-bis[di(3,5-xylyl)phosphino]-1,1'-binaphthyl}[1-(4-methoxyphenyl)-1-(4-methoxyphenyl-kC)-3-methyl-1,2-butanediamine]ruthenium(II),
paraphos=13-[(triphenylmethoxy)methyl]tricyclo[8.2.2.2$^{4,7}$]hexadeca-4,6,10,12,13,15-hexaene-5,11-diyl]bis[diphenylphosphine],
Xyl-Phanephos=4,12-Bis(di(3,5-xylyl)phosphino)-[2.2]-paracyclophane,
P-phos=2,2',6,6'-Tetramethoxy-4,4'-bis(diphenylphosphino)-3,3'-bipyridine,
Xyl-Skewphos=2,4-bis(di-3,5-xylylphosphino)pentane,
tBu=t-butyl group,
Tol=tolyl group,
Xyl=xylyl group,
Me=methyl group The term "er" is the enantiomeric ratio and is the ratio of the percentage of one enantiomer of the alcohol (e.g., the S-enantiomer) to the other enantiomer (i.e., the R-enantiomer). Hydrogenation of ketone 1 was evaluated using 32 commercially available RuCl$_2$(diphosphine)(diamine) complexes (S/C 50) with t-BuOK in IPA (see Table 1 for representative conditions). This initial screen identified RuCl$_2$[(S)-tol-BINAP][(S)-i-Pr-BIMAH] as a suitable catalyst for the reduction of 1 providing (R)-2 in quantitative yield and 98:2 er. Additional screening of solvents revealed RuCl$_2$[(S)-tol-BINAP](ampy) (ampy=2-aminomethylpyridine) in ethanol as another active catalytic system, affording (R)-2 in quantitative yield and 98:2 er. However, upon catalyst loading optimization studies, complete conversion was not achieved at S/C≤1000, which was not economically feasible for scale-up due to the high cost of the catalysts.

TABLE 1

Evaluation of commercial Ru-complexes for the asymmetric hydrogenation of 1.

| Entry | Ru-complex | Conversion (%)$^a$ | er$^b$ |
|---|---|---|---|
| 1 | RuCl$_2$[(R)-BINAP][(R)-daipen] | 11 | — |
| 2 | RuCl$_2$[(R)-Xyl-BINAP][(R)-daipen] | 23 | 5:95 |
| 3 | RuCl$_2$[(R)-BINAP][(R,R)-dpen] | 6 | — |
| 4 | RuCl$_2$[(S)-Tol-BINAP][(S)-i-Pr-BIMAH] | 100 | 98:2 |
| 5 | RuBr$_2$[(S)-Xyl-Skewphos](ampy) | 96 | 8:92 |
| 6 | RuCl$_2$[(R)-Xyl-Phanephos][(S,S)-dpen] | 0 | — |
| 7 | RuCl$_2$[(S)-Xyl-P-Phos][(R)-daipen] | 1 | — |
| 8 | RuCl$_2$[(S)-Paraphos][(R,R)-dpen] | 100 | 79:21 |
| 9 | RuCl$_2$[(S,S)-DIOP][(S)-i-Pr-BIMAH] | 98 | 26:74 |
| 10 | (R)-RUCY ™-Xyl-BINAP | 10 | 17:83 |
| 11 | RuCl$_2$[(S)-Tol-BINAP](ampy) | 100 | 98:2 |

$^a$molar conversion as determined by HPLC;

$^b$recorded as R:S;

$^c$EtOH as solvent Enantiomeric ratios were determined by chiral HPLC;

The R absolute configuration of 2 was determined by chemical correlation to the final product.

At this point, the reaction was evaluated using BIBOP ligands, which we had previously developed for rhodium-catalyzed hydrogenation of functionalized olefins (see W. Tang et al., *Org. Lett.* 2010, 12, 176). RuCl$_2$(BIBOP)(p-cymene) complexes 3 were prepared from BIBOP and [RuCl$_2$(p-cymene)]$_2$ in EtOH/CH$_2$Cl$_2$. To evaluate the efficiency of the new catalytic system, the hydrogenation of 1 was explored in-situ with several diamines (Table 2).

TABLE 2

Evaluation of Ru-BIBOP/diamine complexes in the reduction of 1.

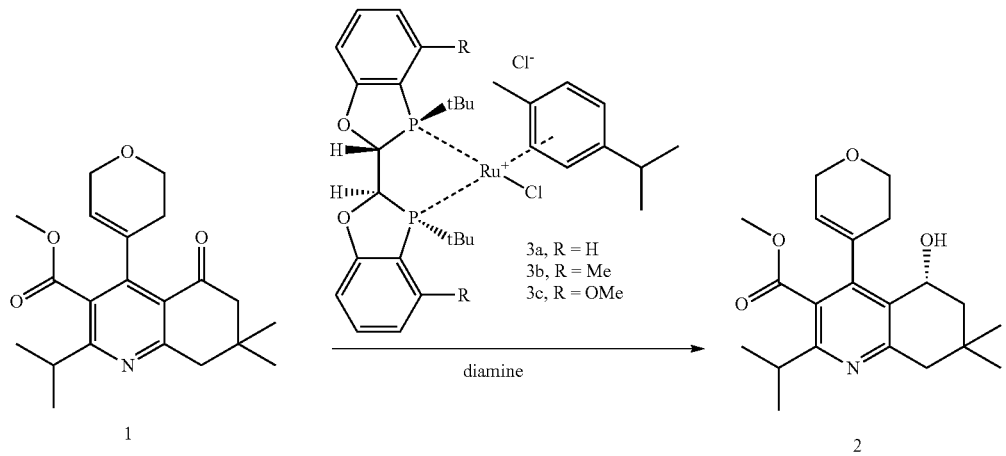

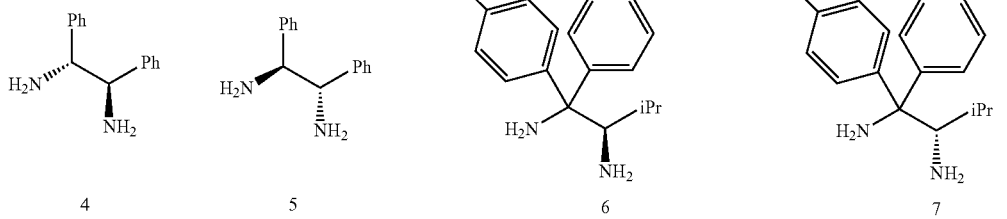

| | 4 | 5 | 6 | 7 |
|---|---|---|---|---|
| 4a: | 0% | | 0% | 0% |
| 4b: | 0% | 100%, 83:17 | 17%, 6:94 | 22% |
| 4c: | 100%, 46:54 | 79%, 26:74 | 6% | 9% |

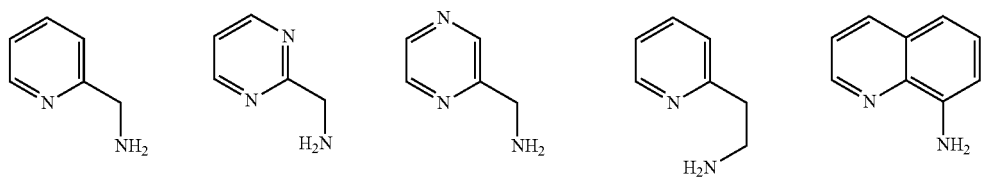

| | 8 | 9 | 10 | 11 | 12 |
|---|---|---|---|---|---|
| 4a: | 100%, 9:91 | | | | |
| 4b: | 100%, 11:89 | | | | |
| 4c: | 100%, >99:1 | 100%, >99:1 | 25%, 99:1 | 47%, 92:8 | 100%, >99:1 |

Conditions: H$_2$ (400 psi), 4-5 mol % precatalyst 3, 4-5 mol % diamine, t-BuOK, IPA, 25° C., 15 h, molar conversion as determined by HPLC; er recorded as R:S As shown in Table 2, the highest enantioselectivities (over 99:1 er) were observed with ampy, 8, 2-aminomethylpyrimidine, 9, and amqui, 12. Interestingly, inverse enantioselectivity was observed when changing the R substituent in the BIBOP ligand from hydrogen (3a) or methyl (3b) to methoxy (3c) with 8 as diamine, going from 9:91 and 6:94 to >99:1 er, respectively. Inverse selectivity effects were also observed with a given phosphine complex 3 and different amines, i.e. 3c provided opposite enantioselectivities with diamines 4 and 5 than 8-12.

To evaluate the reactivity of the most selective catalysts for the reduction of 1, we synthesized the corresponding RuCl$_2$(BIBOP)(diamine) complexes by reaction of 3 with the corresponding diamines in toluene at 110° C. Isomeric mixtures of at least four isomers were observed by $^{31}$P-NMR spectroscopy when using diamines 8, 9 and 12. As reported for other 2-aminomethylpyridine complexes, no differences in reactivity or enantioselectivity were observed regardless of the isomeric ratio of the pre-catalyst mixture. Screening of the premade RuCl$_2$(MeO-BIBOP)(diamine) catalysts along with optimization of the reaction conditions for solvent, pressure and temperature, allowed the synthesis of (R)-2 using RuCl$_2$(MeO-BIBOP)(ampy) at S/C 20,000 under 300 psi of hydrogen on 0.5 kg scale in 98% yield and >99:1 er.

The prepared catalysts were also efficient for asymmetric transfer hydrogenation applications. When 1 was treated with 0.2 mol % 13 and 10 mol % sodium isopropoxide in IPA at 80° C., a 93% yield of (R)-2 and >99:1 er was obtained. Table 3 shows the results of the asymmetric hydrogenation of an exemplary heteroaryl cyclic ketone (ketone 14) of the invention to provide alcohol 15.

TABLE 3

Asymmetric hydrogenation of ketone 14.

| Entry | Ru-complex | Conversion (%)[a] | er[b] |
|---|---|---|---|
| 1 | RuCl$_2$[(R)-BINAP][(R)-daipen] | 98 | 86:14 |
| 2 | RuCl$_2$[(R)-Xyl-BINAP][(R)-daipen] | 100 | 68:32 |
| 3 | RuCl$_2$[(S)-BINAP][(S,S)-dpen] | 100 | 12:88 |
| 4 | RuCl$_2$[(S)-BINAP][(S)-i-Pr-BIMAH] | 100 | 60:40 |
| 5 | RuBr$_2$[(S)-Xyl-Skewphos[ ][(R)-daipen] | 100 | 87:13 |
| 6 | RuCl$_2$[(R)-Xyl-Phanephos][(S,S)-dpen] | 100 | 56:44 |
| 7 | RuCl$_2$[(S)-Xyl-P-Phos][(R)-daipen] | 100 | 92:8 |
| 8 | RuCl$_2$[(S)-Paraphos][(R,R)-dpen] | 100 | 49:51 |
| 9 | RuCl$_2$[(S,S)-DIOP][(S)-i-Pr-BIMAH] | 100 | 49:51 |
| 10 | (R)-RUCY™-Xyl-BINAP | 96 | 35:65 |
| 11 | 3c + 4 | 100 | 1:99 |
| 12 | 3c + 5 | 100 | 10:90 |
| 13 | 3c + 6 | 100 | 5:95 |
| 14 | 3c + 7 | 100 | 3:97 |
| 15 | 3c + 8 | 100 | 59:41 |
| 16 | 3c + 12 | 100 | 90:10 |

[a]molar conversion as determined by HPLC;
[b]recorded as R:S

The new Ru-BIBOP catalysts also proved to be more selective than 34 commercially available complexes in the reduction of 4,5,6,7,8-tetrahydro-5-quinolinone, 14 (see Table 3 for representative examples). Evaluation of commercial complexes allowed up to 92:8 er by using RuCl$_2$[(S)-Xyl-P-Phos][(R)-daipen] (entry 7). The highest enantioselectivities of >97:3 er were obtained when using complex 3c with (R,R)-dpen, 4, or (S)-daipen, 7 (entries 11 and 14). A remarkable inversion of the stereoselectivity was observed when using 3c in combination with 12 (entry 16) instead of diamines 4-7 (entries 11-14). Although some scattered examples of inversion of stereoselectivity can be found in the literature, no general evaluation has been undertaken.[8]

The reduction of other heterocycles to provide isoquinolines 16-17, benzothiophene 18, benzofuranone 19, and pyrazole 20 also resulted in high selectivities (Table 4).

TABLE 4

Asymmetric hydrogenation scope of cyclic ketones of formula (Y1) or alkyl ketones of formula (Y2) using RuCl$_2$(MeO-BIBOP)(diamine).

16
26: 98:2 er
27: 23:77 er 17
97:3 er
20:80 er 18
99:1 er
2:98 er 19
95:5 er
3:97 er 20
26: 97:3 er
27: 6:94 er 21
99:1 er
4:96 er 22
93:7 dr, >99:1 er
>99:1 dr, 6:94 er 23
26: 94:6 er
27: 70:30 er 24
95:5 er
75:25 er 25
95:5 er
72:28 er

Reaction conditions: 0.1-2 mol % RuCl2[2R,2'R,3S,3'S)-MeO-BIBOP](diamine), 0.2 equiv of t-BuOK, IPA, 25° C., 20 h under 400 psi of hydrogen;
The enantiomeric ratios were determined by chiral HPLC and refer to S/R ratios;
Absolute configurations were assigned by comparison of optical rotation with reported data or with authentic samples.

Reaction conditions: 0.1-2 mol % RuCl$_2$[(2R,2'R,3S,3'S)-MeO-BIBOP](diamine), 0.2 equiv of t-BuOK, IPA, 25° C., 20 h under 400 psi of hydrogen; The enantiomeric ratios were determined by chiral HPLC and refer to S/R ratios; Absolute configurations were assigned by comparison of optical rotation with reported data or with authentic samples.

Complete inversion of enantioselectivity was observed in when using pre-made complexes 26 and 27. These catalysts also provided high stereoselectivities of 1-tetralols 21-22. Aryl alkyl ketones such as acetophenone, p-bromoacetophenone and 3-acetylpyridine were also suitable substrates providing 23-25 in enantiomeric ratios of 94:6, 95:5 and 95:5, respectively, when using the dpen complex 26. Interestingly, in the case of the aryl methyl ketones, no inversion of enantioselectivity was observed when using the amqui complex 27.

Examples

General procedure for hydrogenation: Hydrogenation of 28 illustrates the typical reaction procedure: To a mixture of 1-tetralone, 28, (10.0 g, 66.4 mmol) and RuCl$_2$[(2R,2'R,3S,3'S)-MeO-BIBOP](amqui), 27, (1.0 mg, 0.001 mmol, 0.002 mol %) was added isopropanol (40 mL) and a 1 M solution of t-BuOK in tert-butanol (1.33 mL, 1.33 mmol, 0.02 equiv). The autoclave reactor was first purged with nitrogen, then with hydrogen, and then the reaction mixture was stirred at 60° C. under 400 psi of hydrogen for 20 h. After venting the hydrogen gas, the solvent was removed under reduced pressure. The residue was purified by silica-gel column chromatography with ethyl acetate/hexane (0-50%) as eluent to give (R)-1,2,3,4-tetrahydro-1-naphthol, 29, (colorless oil, 9.6 g, 98% yield, 96:4 er). The er of 1,2,3,4-tetrahydro-1-naphthol was determined by HPLC analysis: column, Chiralcel OJ-3, 4.6×150 mm; eluent, heptane/isopropanol (95:5); flow rate, 1 mL/min; column temperature, 25° C.; retention time (tR) of (R)-1,2,3,4-tetrahydro-1-naphthol, 7.45 min (95.8%); tR of (S)-1,2,3,4-tetrahydro-1-naphthol, 5.75 min (4.2%). [α]D=−31.2 (c=2.0, MeOH).

Except for cyclic ketone 1 (describe below), the cyclic ketones of formula (Y1) and alkyl ketones of formula (Y2) are commercially available or can be prepared known methods.

Preparation of cyclic ketone 1: Ketone 1 is prepared according to the method depiction in the Scheme 3 below.

Scheme 3

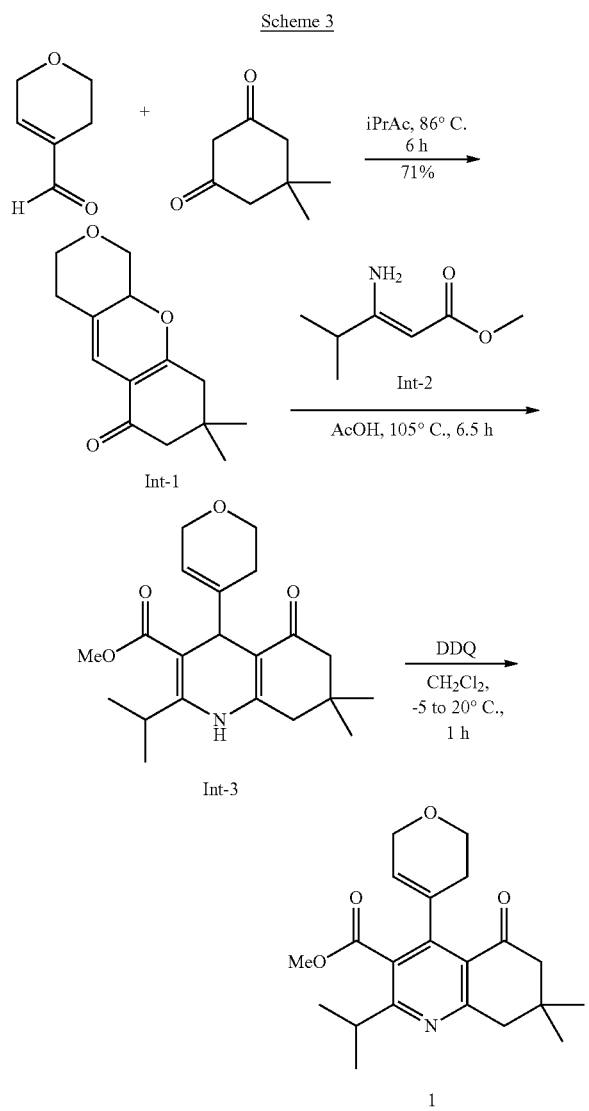

A dried 2L jacket reactor is flushed with argon and then charged with 3,6-dihydro-2H-pyran-4-carbaldehyde (360.3 g, 57.4 wt %, 1.844 mol) and 5,5-dimethyl-cyclohexane-1,3-dione (336.1 g, >99 wt %, 2.398 mol). Isopropyl acetate (iPrAc, 1.05 L) is charged and the mixture is agitated for 10 min at about 20° C. The mixture is charged with 2,6-lutidine (42.96 mL, 0.369 mol) and then is agitated at reflux (about 90° C.) for 5.5 h with a water separator or Dean-Stark apparatus attached. The reaction is monitored by HPLC analysis. After completion of the reaction, the mixture is cooled to 20° C. and iPrAc (600 mL) is charged followed by aqueous hydrochloric acid (655 mL, 1 mol/L), and the mixture is agitated for 15 min. The aqueous layer is removed and the organic phase is washed with aqueous sodium hydroxide (655 mL, 2 M) and water (655 mL). The organic phase is concentrated to about 650 mL under vacuum and cooled to about 6° C. Heptane (2 L) is charged in over 1 h and the mixture stirred for 14 h at about 6° C. The slurry is filtered and the wet cake is washed with heptane (600 mL) and dried to yield Int-1 as a yellow solid (315.33 g, 96.6 wt %) in 70.5% yield.

A 2 L jacketed reactor is charged ammonium acetate (668 g, 8.67 mol) and the reactor is flushed with argon. Then 4-methyl-3-oxopentanoate (500 g, 3.47 mols) is charged followed by methanol (1.0 L). The mixture is agitated at 55° C. for 5 h and concentrated in vacuo to about 1 L and then cooled to about 20° C. A solution of iPrAc (1.5 L) is added and the organic phase is washed with water (2×1.0 L). The organic phase is concentrated to provide methyl 3-amino-4-methyl-pent-2-enoate (Int-2) as yellow oil (560 g, 68 wt %) in 76% yield, which is used directly in next step.

A dried 2 L jacket reactor is charged with Int-2 (193.5 g, 97.0 wt %, 0.801 mol) and Int-2 (208.9 g, 71.4 wt %, 1.04 mol), and the reactor is flushed with argon. The reaction is charged with acetic acid (AcOH, 950 mL) and the mixture is agitated at 105 to 110° C. for 7 h. The reaction is monitored by HPLC analysis. The mixture is cooled to about 20° C. and agitated for 1 h (significant amount of solids may crystallize out). Water (1.68 L) is charged to the mixture over 1.5 h to form a slurry and stirred for about 3 h. The slurry is filtered and the wet cake is washed with heptane (600 mL) and dried under vacuum at 75° C. for 3 days to yield Int-3 as a yellow solid (170 g, 98.6 wt %) in 58% yield.

A dried 2 L jacketed reactor is charged with Int-3 (130 g, 93.4 wt %, 0.338 mol) and methylene chloride (DCM) (800 mL), and the mixture is stirred and cooled to about 5° C. 2,3-dichloro-5,6-dicyano-p-benzoquinone (DDQ, 79.0 g, 0.348 mol) is charged as a slurry in DCM (600 mL) while keeping the temperature at 5 to 10° C. The vessel is rinsed with DCM (2×100 mL) and charged to the reaction mixture. The reaction mixture is stirred for 30 min at 5 to 10° C. and then warmed to about 18 to 22° C. and agitated for 30 min. The reaction is monitored by HPLC analysis. The reaction mixture is concentrated under vacuum to ~⅓ volume (~600 mL) and chased with iPrAc (1.5 L) at about 50° C. to 80° C. The mixture is cooled to about 20° C. and charged with iPrAc (1.2 L), and the organic phase is washed with 1 M aqueous NaOH (1.5 L) and water (2×1.0 L). The organic solvents are concentrated under vacuum to about 1 L and the solution then passed through a silica plug. The silica plug is rinsed with iPrAc (500 mL) and the combined filtrates are concentrated to provide 1 as a solid (122 g, 93.2 wt %) in 93% yield.

What is claimed is:

1. A compound of formulae (Ia) and (Ib):

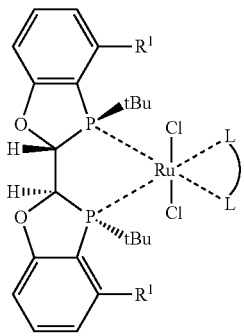

Ia

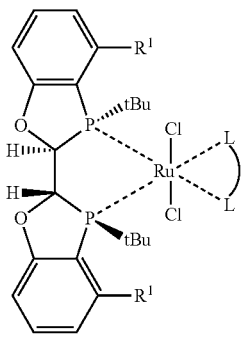

Ib wherein $R^1$ are both the same and selected from —H, —$CH_3$ and —$OCH_3$; and the moiety L⌒L represents a diamine ligand selected from the group consisting of compounds 4, 5, 6, 7, 8, 9, and 12:

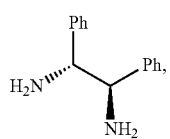

4

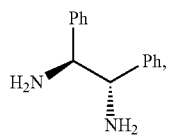

5

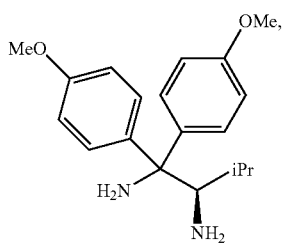

6

-continued

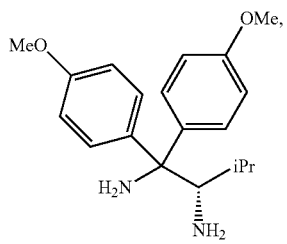

7

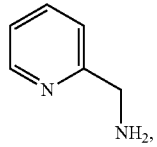

8

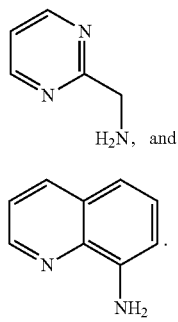

9 and

12

2. The compound of formula (Ia) or (Ib) according to claim 1, wherein $R^1$ is —H.

3. The compound of formula (Ia) or (Ib) according to claim 1, wherein $R^1$ is —$CH_3$.

4. The compound of formula (Ia) or (Ib) according to claim 1, wherein $R^1$ is —$OCH_3$.

5. The compound of formula (Ia) or (Ib) according to claim 1, wherein the diamine ligand is compound 4.

6. The compound of formula (Ia) or (Ib) according to claim 1, wherein the diamine ligand is compound 5.

7. The compound of formula (Ia) or (Ib) according to claim 1, wherein the diamine ligand is compound 6.

8. The compound of formula (Ia) or (Ib) according to claim 1, wherein the diamine ligand is compound 7.

9. The compound of formula (Ia) or (Ib) according to claim 1, wherein the diamine ligand is compound 9.

10. The compound of formula (Ia) or (Ib) according to claim 1, wherein the diamine ligand is compound 12.

11. The compound of formula (Ia) or (Ib) according to claim 10, wherein $R^1$ is —$OCH_3$.

12. The compound of formula (Ia) or (Ib) according to claim 1, wherein the diamine ligand is compound 8.

13. The compound of formula (Ia) or (Ib) according to claim 12, wherein $R^1$ is —H.

14. The compound of formula (Ia) or (Ib) according to claim 12, wherein $R^1$ is —$CH_3$.

15. The compound of formula (Ia) or (Ib) according to claim 12, wherein $R^1$ is —$OCH_3$.

16. The compound of formula (Ia) according to claim 1.

17. The compound of formula (Ib) according to claim 1.

18. Compound 13:
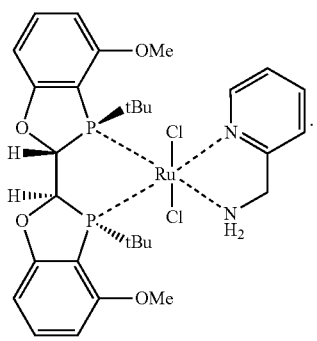
19. Compound 27:
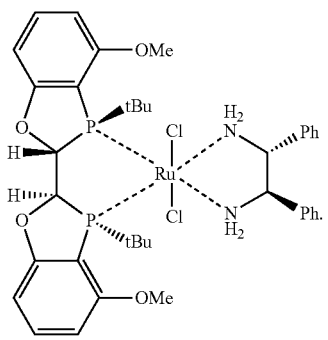
20. Compound 28:
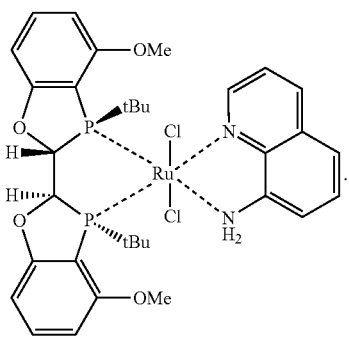
21. A process for making a chiral alcohol of formula X1, the process comprising reacting a ketone of formula Y1 with hydrogen in the presence of a ruthenium compound, wherein the ketone of formula Y1 and the corresponding chiral of formula X1 are as defined below:

| Ketone (Y1) | Alcohol (X1) |
|---|---|
| 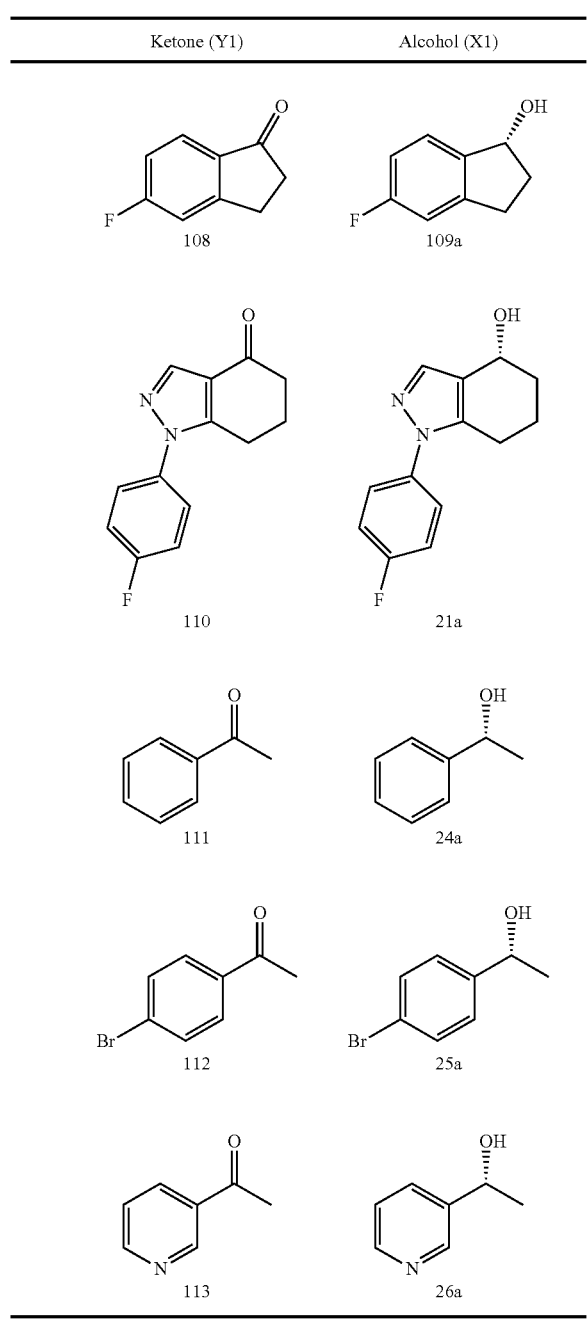 | |

Ketone (Y2)

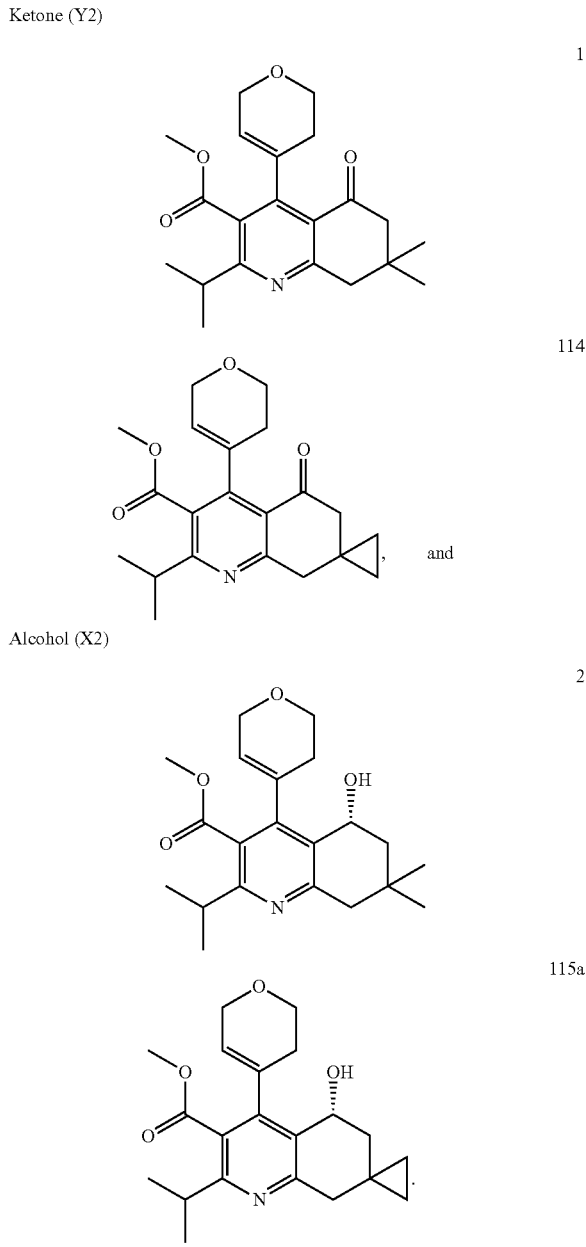

Alcohol (X2)

and the ruthenium compound is (a) the compound of formula (Ia) as defined in claim 1, wherein $R^1$ is —OCH$_3$, and the diamine ligand is compound 12; or (b) the compound of formula (Ib) as defined in claim 1, wherein $R^1$ is —OCH$_3$, and the diamine ligand is compound 4, 5, 6 or 7.

22. A process for making a chiral alcohol of formula X2, the process comprising reacting a ketone of formula Y2 with hydrogen in the presence of a ruthenium compound, wherein the ketone of formula Y2 and the corresponding chiral of formula X2 are as defined below:

and the ruthenium compound is (a) the compound of formula (Ia) as defined in claim 1, wherein $R^1$ is —CH$_3$, and the diamine ligand is compound 5;

(b) the compound of formula (Ia) as defined in claim 1, wherein $R^1$ is —OCH$_3$, and the diamine ligand is compound 8, 9 or 12; or (c) the compound of formula (Ib) as defined in claim 1, wherein $R^1$ is —H or —CH$_3$, and the diamine ligand is compound 8.

23. A process for making a chiral alcohol of formula X3, the process comprising reacting a ketone of formula Y3 with hydrogen in the presence of a ruthenium compound, wherein the ketone of formula Y3 and the corresponding chiral of formula X3 are as defined below:

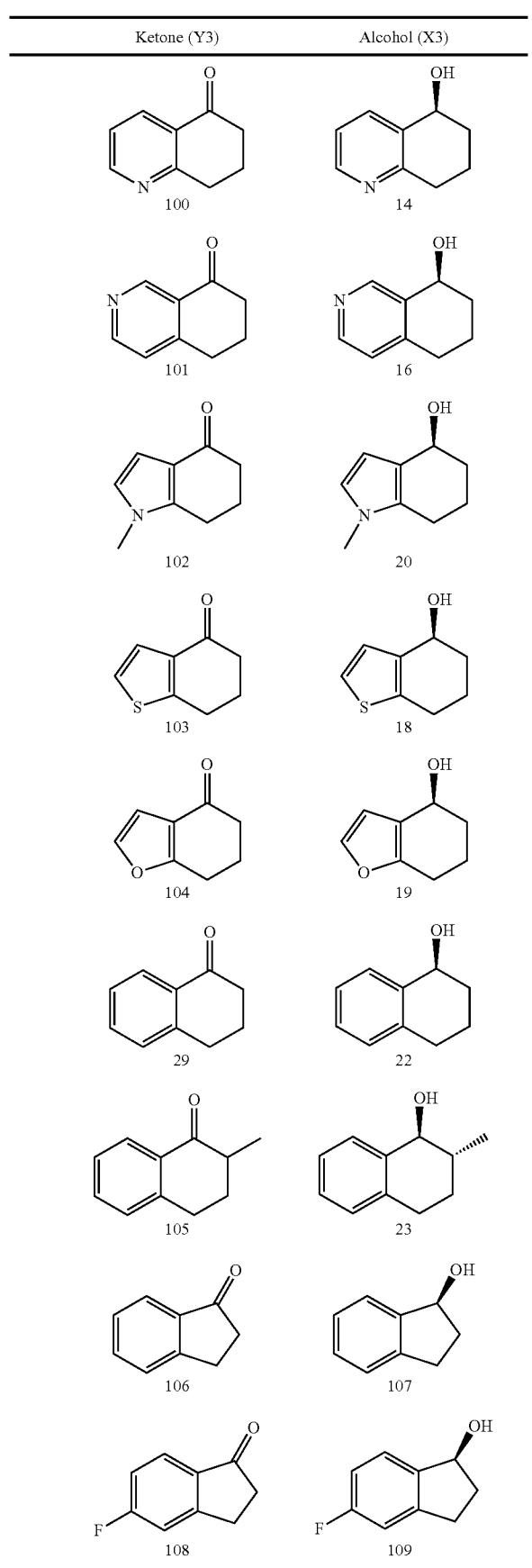

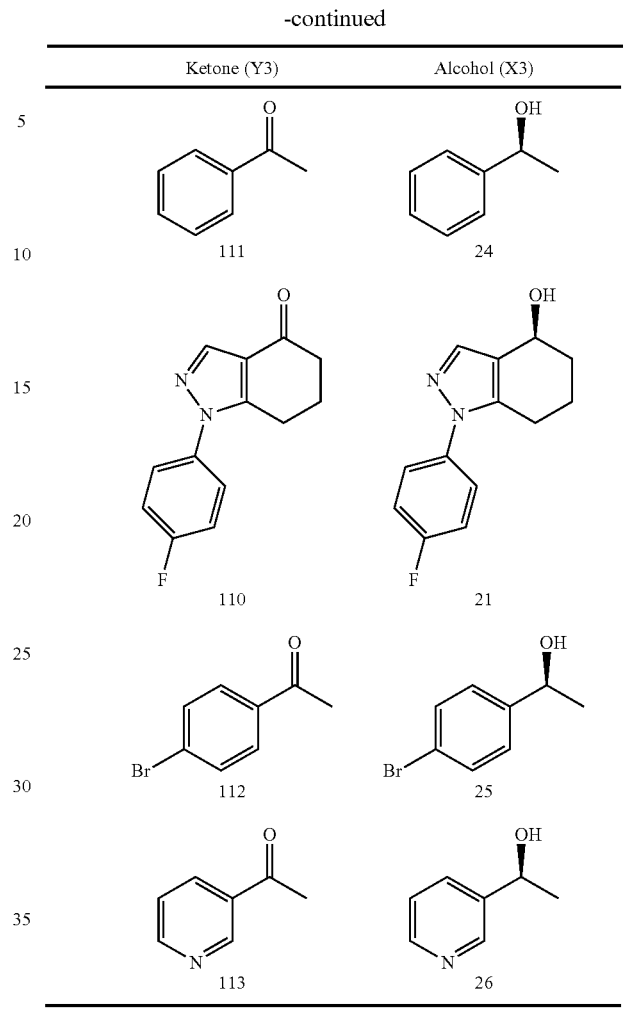

and the ruthenium compound is (a) the compound of formula (Ib) as defined in claim 1, wherein $R^1$ is —$OCH_3$, and the diamine ligand is compound 12; or (b) the compound of formula (Ia) as defined in claim 1, wherein $R^1$ is —$OCH_3$, and the diamine ligand is compound 4, 5, 6 or 7.

24. A process of making a chiral alcohol of formula X4, the process comprising reacting a ketone of formula Y4 with hydrogen in the presence of a ruthenium compound, wherein the ketone of formula Y4 and the corresponding chiral of formula X4 are as defined below:

Ketone (Y4)

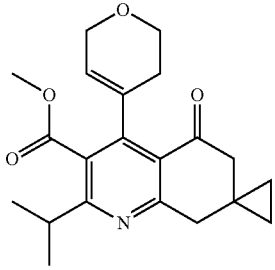 [SMILES: COC(=O)c1c(C(C)C)nc2c(c1C1=CCOCC1)C(=O)CC1(CC1)C2]
Alcohol (X4)
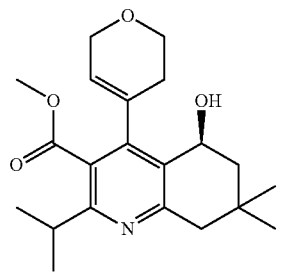
2a
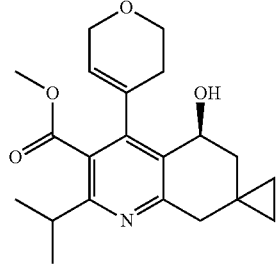
and
the ruthenium compound is
(a) the compound of formula (Ib) as defined in claim 1, wherein $R^1$ is —CH$_3$, and the diamine ligand is compound 5;
(b) the compound of formula (Ib) as defined in claim 1, wherein $R^1$ is —OCH$_3$, and the diamine ligand is compound 8, 9 or 12; or
(c) the compound of formula (Ia) as defined in claim 1, wherein $R^1$ is —H or —CH$_3$, and the diamine ligand is compound 8.
* * * * *